United States Patent [19]

Renard et al.

[11] Patent Number: 4,837,446

[45] Date of Patent: Jun. 6, 1989

[54] APPARATUS AND PROCESS FOR TESTING UNIFORMITY OF PULP

[75] Inventors: Jean J. Renard, Mobile, Ala.; David M. Hanson, Cornwall, N.Y.

[73] Assignee: International Paper Company, Purchase, N.Y.

[21] Appl. No.: 175,516

[22] Filed: Mar. 31, 1988

[51] Int. Cl.[4] .......................................... G01N 21/64
[52] U.S. Cl. .................... 250/461.1; 250/458.1; 250/459.1
[58] Field of Search ............... 250/461.2, 461.1, 459.1, 250/458.1

[56] References Cited

U.S. PATENT DOCUMENTS

| | | | |
|---|---|---|---|
| 3,151,204 | 9/1964 | Stacy | 88/14 |
| 3,518,003 | 6/1970 | Meyn | 356/116 |
| 3,674,434 | 7/1972 | Pottenger | 23/230 R |
| 3,704,950 | 12/1972 | Rosencranz | 356/73 |
| 3,710,933 | 1/1973 | Fulwyler et al. | 209/3 |
| 3,824,402 | 7/1974 | Mullaney et al. | 250/565 |
| 3,850,525 | 11/1974 | Kaye | 356/73 |
| 3,917,945 | 11/1975 | Sema et al. | 250/301 |
| 4,008,397 | 2/1977 | Zdrodowski | 250/373 |
| 4,066,492 | 1/1978 | Hill | 162/49 |
| 4,171,916 | 10/1979 | Simms et al. | 356/366 |
| 4,172,227 | 10/1979 | Tyrer et al. | 250/461.2 |
| 4,318,180 | 3/1982 | Lundqvist et al. | 364/555 |
| 4,342,618 | 8/1982 | Karnis et al. | 162/49 |
| 4,345,913 | 8/1982 | Jönsson | 23/230 R |
| 4,402,604 | 9/1983 | Nash | 356/237 |
| 4,426,154 | 1/1984 | Steen | 356/73 |
| 4,441,960 | 4/1984 | Karnis et al. | 162/49 |
| 4,514,257 | 4/1985 | Karlsson et al. | 162/49 |
| 4,540,468 | 9/1985 | Genco et al. | 162/49 |
| 4,548,498 | 10/1985 | Folestad et al. | 356/318 |
| 4,554,051 | 11/1985 | Danforth | 162/49 |
| 4,573,796 | 3/1986 | Martin et al. | 356/318 |
| 4,643,566 | 2/1987 | Ohe et al. | 356/72 |

FOREIGN PATENT DOCUMENTS 1176839 10/1984 Canada .

OTHER PUBLICATIONS

John A. Steinkamp and David L. Carlson, "Identification of Single Cells by Fluorescent and Darkfield Optical Techniques", *8th ISA Biomedical Sciences Instrumentation Symposium*, Denver, CO, U.S. (May 4–6, 1970) pp. 10–17.
Title: "Applying Waste Liquor Fluorescence to Control Pulp Quality", Authors: W. J. Bublitz and D. C. Wade, Publication: *Svensk Paperstidning*, Nov. 18, (1979), pp. 535–538.

*Primary Examiner*—Janice A. Howell
*Assistant Examiner*—Constantine Hannaher
*Attorney, Agent, or Firm*—Luedeka, Hodges & Neely

[57] ABSTRACT

An apparatus and process for testing the uniformity of a papermaking pulp with respect to the lignin associated with individual fibers comprising substantially simultaneous analysis of individual fiber length and fluorescence of the lignin associated with such individual fiber. The ratio of the lignin mass over the fiber length has been found to be proportional to the Kappa Number.

17 Claims, 1 Drawing Sheet

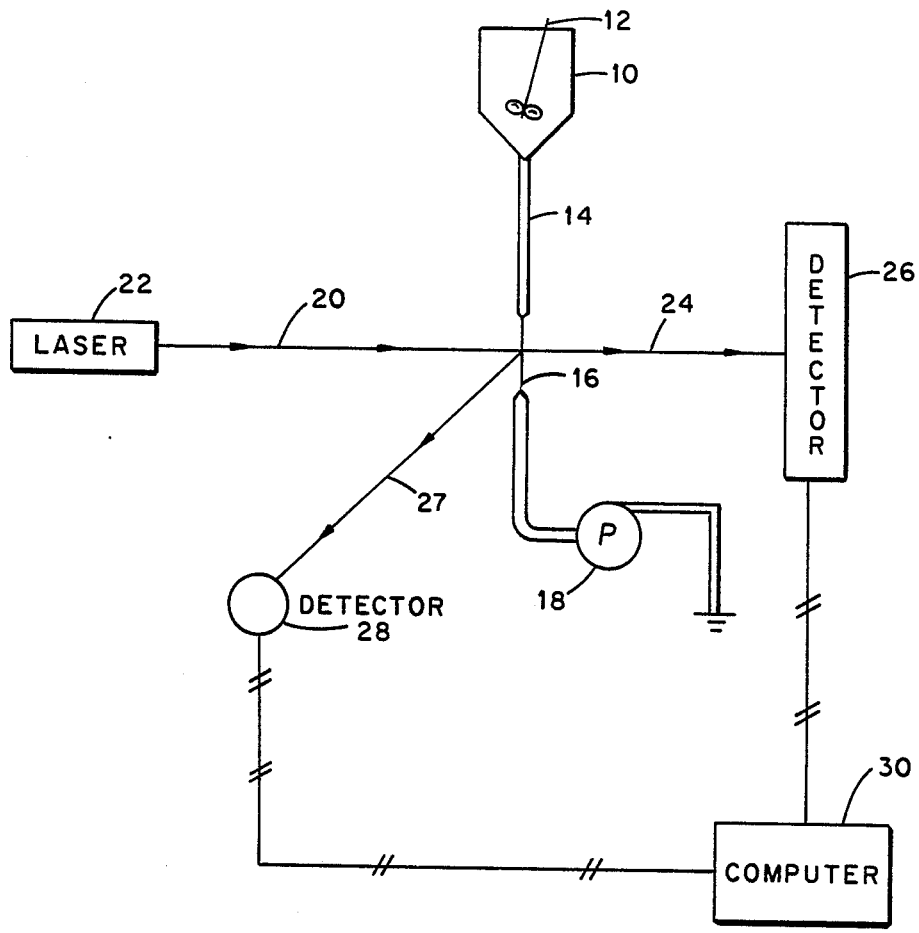

APPARATUS AND PROCESS FOR TESTING UNIFORMITY OF PULP

FIELD OF THE INVENTION

This invention relates to the testing of papermaking pulps for uniformity with respect to the lignin associated with the fibers of the pulp.

Pulping, as the term is used in papermaking, refers to the conversion of wood chips into separate fibers by the chemical reaction between lignin found in the wood chips and the active chemicals in a cooking liquor. Pulping processes commonly are of the kraft type or the sulfite type. In each of these, and other, types of pulping processes, the concept is to separate the fibers by breaking down the lignin that acts as a binder that holds the fibers one to another.

The reactions of lignin with the cooking liquors are complex and not fully understood. Briefly, the sulfite process forms a sulphonic acid of the lignin and the kraft process an alkali- or thio-lignin. These products are soluble and are largely removed from the pulp in subsequent processing. The facet of lignin behavior that is of importance in pulp quality is the nature and location of the residual few percent of lignin that remains associated with the individual fibers.

In the prior art it is customary to test the lignin content of the cooking liquors within the chip digester and to use this determination as a measure of the effectiveness of the ongoing pulping operation. One major problem with this prior art testing lies in the fact that when one tests the cooking liquors, one is determining only the quantity of lignin that has collected in the liquor. It is only by reference back to total lignin quantity contained within the wood chips that one is able to determine the effectiveness of the delignification process using these prior art tests.

Following a pulping operation, it is common in many wood pulps to pass the fibers through a bleaching process. In the present context, bleaching refers to chlorination of the wood pulp and generally comprises the first stage of most bleaching sequences. The intention of chlorination is to de-lignify rather than simply to decolorize pulp, and therefore chlorination may be said to constitute an extension of the pulping process. Numerous investigations of the chlorination process have failed to provide a complete understanding of the mechanism of pulp chlorination. While it is generally agreed that lignins represent polymeric materials composed of various phenol propane units bonded together by a complex system of ether and carbon-to-carbon linkages, the nature of this bonding system has remained a matter of more or less well-founded speculation. Under the conditions of technical chlorination, "residual lignin" in the unbleached pulp undergoes a great variety of reactions that finally lead to its degradation into water-and-alkali-soluble fragments.

Predicting the bleachability of pulp in the prior art has been by one or more of the several available tests such as the Permanganate Number (TAPPI method T-214), or the Kappa Number (TAPPI method T-236), Roe Chlorine Number (TAPPI method 202), etc. Each of these tests is designed to determine the quantity of lignin present in the pulp fibers as a group and provides an indication of the total bleach requirement (chlorine demand of the pulp) in the chlorination stage. Possibly, the most commonly used of these tests is the Kappa Number which is defined as the quantity of potassium permanganate consumed by one gram of oven dry pulp under specified conditions. Notably, the Kappa Number Test, as well as the other Tests noted, require extracting a representative sample of pulp, separating the pulp fibers from the cooking liquor, drying the pulp to oven dry conditions, resuspending the fibers, and treating this new mixture with one or more special reagents such as 20 mmol/l solution of potassium permanganate, all under strict laboratory conditions and requiring skilled laboratory technicians.

None of these tests, however, provide a measure of the "uniformity" of the pulp. "Uniformity" as referred to herein, is defined as the constancy of the properties of the individual fibers constituting the pulp. It is this uniformity, or the lack thereof, that enables or prevents one from predicting the optimum operating parameters in the various papermaking procedures, e.g. bleaching, refining, forming, etc., or predicting the properties of the paper product. Only one test for measuring uniformity of pulp is known by the present invetors to have been used heretofore. Such test is known as the "Tichy and Procter" Test and involves a density gradient column. This test is time consuming, requires a skilled technician, and, relying on a counting technique, is inherently inaccurate.

In Canadian Patent No. 1,176,839, there is described a process and apparatus for determining the length of individual fibers using shadow measurements. This patent makes no reference to lignin analysis.

The present inventor has discovered a novel process for testing the uniformity of pulp as respects the lignin associated with the individual fibers of the pulp wherein the test is easily carried out under field conditions by relatively unskilled persons and is useful as an indicator of digester operation as well as a predictor of pulp bleachability and performance on the paper machine.

Accordingly, it is an object of the present invention to provide a process for testing the uniformity of a pulp as respects the lignin content of the individual fibers of the pulp.

It is another object to provide a process of the type described which is useful as an indicator of pulp digester operation as well as a predictor of pulp bleachability and performance on a paper machine.

It is another object of the invention to provide a process of the type referred to above which is capable of being performed in the field as opposed to requiring laboratory conditions.

It is another object of the invention to provide a process of the type described which does not require a skilled laboratory technician or the equivalent for carrying out the process.

It is another object to provide apparatus for carrying out the process of the invention.

Other objects and advantages of the invention will be recognized from the following disclosure including the drawing which is a schematic representation of apparatus for carrying out the process of the present invention.

SUMMARY OF THE INVENTION

In accordance with the present invention, a sample of the pulp, representative of the pulp as a whole, is taken. This sample is diluted, agitated thoroughly, and directed into a flowing stream. In the preferred form, the flowing stream comprises movement of the sample through a tube having a capillary section whose internal diameter is slightly larger than the maximum diameter of individual fibers in the pulp such that the fibers are forced to flow through the capillary section one at a time. A beam of light, preferably a laser beam, is directed into the flowing stream at substantially a right angle thereto. Simutaneously, as a fiber passes through the capillary section of the tube, the fiber is caused to cast a shadow onto an array of diodes, and is caused to fluoresce, the fluorescence being emitted at all angles to the incident beam. The fluorescent beam is monitored, commonly at right angles to the incident beam, along with the length of the shadow of the fiber. The electronic signals representative of the length of the fiber and of the intensity of the fluorescence of the fiber are processed to provide a measurement of the concentration of lignin on individual ones of the fibers.

Unexpectedly, the present inventors have found that dividing the mass of the lignin as determined by the fluorescence of the lignin on the individual fiber by the length of the same fiber provides a value which is directly related to the Kappa number of the pulp. Therefore, the results of the present process can be expressed in terms of the familiar Kappa Number.

Referring specifically to FIG. 1, a sample of pulp which has been properly diluted is stored in a tank 10 where it is agitated as by a stirrer 12 and thereafter caused 15 to flow downwardly through a tube 14 which has a capillary tube section 16. Preferably, the internal diameter of the capillary tube section 16 has an internal diameter between 1.0 and 0.01 mm which insures a flow of single fibers through the section. The flow of the pulp sample from the tank 20 through the capillary section is effected as by a pump 18, preferably of the peristolic or controlled vacuum type.

A beam of coherent monochromatic light such as that generated by an argon laser 22 is directed at a right angle into the capillary section 16. When a paper fiber is present within the capillar section and is disposed in the beam 20, the fiber blocks a portion of the beam 20 with the remainder thereof forming a back scatter beam at 24 which is receivd by an array 26 of diodes. The same fiber, when contacted by the beam 20 will fluoresce to the extent of the quantity of lignin present on the fiber to generate a further beam 27 that emanates from the capillary section 16 and is detected at a right angle to the incident beam 20. This fluorescent beam 27 is detected as by a photocell 28. The values detected by the diode array 26 and by the photocell 28 are input into a computer 30 within which the length of the shadow of the fiber within the capillay section, hence the length of the fiber itself, is calculated. Further, within the computer the intensity of fluorescence detected by the photocell 28 is compared to intensity standards of known lignin quantities to determine the mass of lignin on the individual fiber under observation. As desired, the output from the computer may be in terms of the length of the fiber, the mass of lignin on the fiber, or in such other format as desired. As noted above, in particular, it has been found useful to divide the mass of lignin on the fiber by the length of the fiber to provide a concentration value for the lignin on the individual fiber. It has been found by the present inventors that this concentration value is directly proportional to the Kappa Number for the pulp in question and therefore this output of the computer can be expressed in terms of the Kappa Number which is very familiar to papermaking personnel and useful in pedicting bleachability of the pulp.

Accordingly, it will be recognized that the mass of lignin on the individual fibers, when compared one to another, provides an indication of the effectiveness of operation of the digester from which the pulp sample was taken. For example, if individual fibers have inconsistent values of lignin mass, it is an indication that the wood chips may not be reacting uniformly with the cooking liquor within the digester. Thereupon the operator can examine the operating parameters of the digester to determine which one or ones of these operating parameters may be out of range and causing the nonuniform reactivity of the cooking liquor with the wood chips. In like manner, the mass of lignin on the individual fibers is an indicator of the degree of completeness of the chemical reaction taking place within the digester. Specifically, if substantially all of the fibers have very little lignin present thereon, it is an indication that the digesting process is approaching or has reached its end point.

In the preferred embodiment, the pulp in the stirred tank is a very dilute slurry, typically having a consistency of less than about 0.01 percent, i.e., less than one hundred milligrams of dry fiber in one thousand grams of water. A constant flow rate of pulp slurry through the tube is insured by the peristolic pump. The reduced capillary section of the tube is provided with an internal diameter of between about 1.0 and 0.01 millimeters. This insures a flow of single fibers through the capillary section, thereby making it possible to measure individual fibers.

The light source as indicated is preferably an argon laser. The incident laser beam preferably is polarized and has a wave length of about 488 mm. Although a laser is preferred, because of the ease of focusing, monochromaticity and intensity of the resulting fluorescence, any light source emitting photons with energy capable of inducing lignin fluorescence can be used. Likewise, the incident wavelength is not limited to 488 mm as indicated to be preferable, but rather any incident wavelength inducing a measurable fluorescence specific to the lignin and intensity proportional to the lignin mass is acceptable. Measurement of the emitted fluorescence at 574 nm is chosen because it is at this wavelength that the maximum intensity of fluorescence is developed. Other wavelengths of the emitted fluorescence that are measurable and which are proportional to the intensity of the fluorescence are acceptable as are the collection of wavelengths comprising the fluorescence effect.

Within the computer the length and fluorescence intensity values of the individual fibers are stored, as is the number of fibers analyzed. From these data one can readily determine how many or what percentage of analyzed fibers exhibit lignin concentrations within selected ranges, for example. Other related analyses of the collected data will be recognized as being available, such as extrapolation of the lignin mass data from individual fibers in the sample to provide a measure of the total lignin in the pulp from which the sample was taken. Especially important in the predicting of bleachability of the pulp is the lignin mass remaining associated with the individual fibers at the conclusion of the digesting operation. It is this lignin mass that the chlorine (or other bleaching agent) will be required to attack in the bleaching operation and a knowledge of such lignin mass can be used to predict the chlorine demand to carry out the desired bleaching. Other uses and advantages of the data collected by the present process will be apparent to one skilled in the art. Also, it will be understood that the invention is capable of numerous modifications, rearrangements and substitutions of parts without departing from the scope of the invention as defined by the following claims.

What is claimed is:

1. A process for determining the uniformity of papermaking pulp with respect to the lignin content associated with the fibers of said pulp comprising the steps of:
    selecting a sample of said pulp,
    adjusting the concentration of fibers within said sample to a value less than about 100 milligrams of dry fiber to 1000 grams of water,
    agitating said sample to disperse said fibers within said sample,
    forming said sample into a flowing stream which includes individual fibers of said pulp suspended therein,
    directing a beam of substantially monochromatic light into said stream to cause individual ones of said fibers moving through said beam to cast a length shadow and to cause lignin associated with individual ones of said fibers to fluoresce,
    detecting said length shadow for individual ones of said fibers,
    detecting the intensity of fluorescence of individual ones of said fibers,
    correlating the length shadow value of a particular fiber with the fluorescence of the same fiber.

2. The process of claim 1 and including the step of computing the concentration of lignin per unit of fiber length.

3. A process for testing the uniformity of pulp as respects the lignin content of the individual fibers thereof comprising the steps of:
    collecting a representative sample of said pulp,
    adjusting the concentration of said sample to less than about 100 mg of dry fiber in 1000 g of water, forming said sample into a flowing stream having a cross-sectional dimension slightly greater than the cross-sectional dimension of individual ones of said fibers of said pulp such that individual ones of said fibers are caused to move length wise with the direction of flow of said stream,
    directing a substantially monochromatic polarized beam of light into said stream at substantially a right angle to the direction of flow of said stream, said beam having a wave length of about 488 nm, whereby lignin associated with individual ones of said fibers is caused to fluoresce and individual fibers are caused to cast a length shadow,
    capturing the length dimensions of the shadow of each fiber passing through said beam of light,
    capturing the magnitude of the fluorescence of each fiber at a wave length of about 574 nm substantially simultaneously with the capture of its length dimension.

4. The process of claim 3 and including the step of converting said magnitude of fluorescence to a mass of lignin.

5. The process of claim 4 and including the steps electronically dividing the lignin mass value of each fiber by the captured length dimension of such fiber, and displaying the quotient so obtained.

6. A process for determining the uniformity of papermaking pulp with respect to the lignin content associated with the fibers of said pulp comprising the steps of:
    directing a substantially coherent beam of substantially monochromatic light into a flowing stream of said pulp containing discrete dispersed ones of said fibers, said beam of light having a wavelength suitable to fluoresce lignin,
    detecting the magnitude of fluorescence of lignin associated with individual ones of said fibers.

7. The process of claim 6 including the further steps of:
    substantially simultaneously analyzing the length of said individual ones of said fibers, and
    correlating said magnitude of fluorescence with said length of said individual ones of said fibers to provide a measure of the concentration of lignin associated with individual ones of said fibers.

8. The apparatus of claim 6 wherein the wavelength of said beam of light incident upon said flowing stream is about 488 nm.

9. The apparatus of claim 8 wherein the wavelength of detected fluorescence is about 574 nm.

10. An apparatus for measuring the fluorescence and length of fibers that fluoresce the presence of light of at least one frequency, comprising:
    means defining a sample volume,
    transport means for disposing individual ones of the fibers in the sample volume,
    illuminating means for generating and directing a beam of light onto the sample volume and the fibers present within said sample volume,
    said beam of light having at least one frequency that will cause the fibers to fluoresce at a fluorescent frequency,
    first optical detector means for observing the fibers in said sample volume and for generating a length signal corresponding to the length of individual fibers in said sample volume;
    second optical detector means disposed to receive fluorescent light produced by the fibers in said sample volume and for generating a fluorescence signal corresponding to the intensity of the fluorescent light from the fibers, and
    processing means for receiving the length signal and the fluorescence signal and for producing a comparison signal corresponding to a comparison of the fluorescent light produced by the fiber to the length of the fiber.

11. The apparatus of claim 10 wherein said first optical detector is disposed to receive forward light scattering produced when the light beam strikes the fibers in said sample volume.

12. The apparatus of claim 10 wherein said second optical detector is disposed in a light path from said sample volume that is substantially perpendicular to the path of the beam of light from said illuminating means as it passes through said sample volume.

13. The apparatus of claim 10 wherein said means defining a sample volume comprises at least a capillary tube having a cross-sectional diameter that is within the range of 1.0 mm to 0.01 mm.

14. The apparatus of claim 10 wherein said processing means is a computer that compares the magnitude of the fluorescence signal to the length of the fibers.

15. Apparatus for determining the uniformity of papermaking pulp with respect to the concentration of lignin associated with the fibers of said pulp comprising:
    means containing a sample of said pulp including substantial numbers of discrete fibers dispersed in a liquid,
    pump means,
    conduit means leading from said sample containing means to said pump means for conveying said fibers from said sample containing means to said pump, means defining a length of reduced cross-sectional area of said conduit interposed in the length thereof, a source of substantially coherent and substantially monochromatic light incident upon said reduced cross-sectional area of said conduit, said light being of a wavelength suitable to fluoresce lignin associated with said fibers moving through said conduit, and means detecting the magnitude of fluorescence of lignin associated with individual fibers.

16. The apparatus of claim 15 including means detecting the shadow length of a fiber within said beam of light substantially simultaneously with the detection of fluorescence associated with such fiber, and means correlating said detected magnitude of fluorescence and said shadow length of individual fibers.

17. The apparatus of claim 15 wherein the wavelength of said incident beam of light is about 488 nm and the wavelength of the detected fluorescence is about 574 nm.

* * * * *